US009026386B2

(12) United States Patent
Jiang

(10) Patent No.: US 9,026,386 B2
(45) Date of Patent: May 5, 2015

(54) MATERIAL PROPERTY TESTING DEVICES WITH CAPABILITIES OF MONITORING ENERGY-CONSUMPTION AND DETECTING THE ENVIRONMENT

(76) Inventor: Yunzhong Jiang, JiNan (CN)

( * ) Notice: Subject to any disclaimer, the term of this patent is extended or adjusted under 35 U.S.C. 154(b) by 520 days.

(21) Appl. No.: 13/502,302
(22) PCT Filed: Mar. 8, 2011
(86) PCT No.: PCT/CN2011/000367
§ 371 (c)(1), (2), (4) Date: Jun. 21, 2012
(87) PCT Pub. No.: WO2012/058853
PCT Pub. Date: May 10, 2012

(65) Prior Publication Data
US 2012/0271577 A1 Oct. 25, 2012

(30) Foreign Application Priority Data

| Nov. 5, 2010 | (CN) | 2010 1 0532436 |
| Nov. 5, 2010 | (CN) | 2010 1 0532439 |
| Nov. 5, 2010 | (CN) | 2010 1 0532562 |
| Nov. 5, 2010 | (CN) | 2010 1 0532728 |
| Nov. 5, 2010 | (CN) | 2010 2 0592238 U |
| Nov. 5, 2010 | (CN) | 2010 2 0592239 U |
| Nov. 5, 2010 | (CN) | 2010 2 0592326 U |
| Nov. 5, 2010 | (CN) | 2010 2 0592327 U |
| Nov. 5, 2010 | (CN) | 2010 2 0592404 U |
| Nov. 5, 2010 | (CN) | 2010 2 0592436 U |
| Nov. 5, 2010 | (CN) | 2010 2 0592440 U |
| Nov. 5, 2010 | (CN) | 2010 2 0592490 U |
| Nov. 5, 2010 | (CN) | 2010 2 0592549 U |
| Nov. 5, 2010 | (CN) | 2010 2 0592671 U |
| Nov. 5, 2010 | (CN) | 2010 2 0592924 U |
| Nov. 5, 2010 | (CN) | 2010 2 0653911 U |
| Nov. 5, 2010 | (CN) | 2010 2 0653913 U |
| Nov. 5, 2010 | (CN) | 2010 2 0653914 U |
| Nov. 5, 2010 | (CN) | 2010 2 0653945 U |
| Nov. 5, 2010 | (CN) | 2010 2 0653948 U |
| Nov. 5, 2010 | (CN) | 2010 2 0653952 U |
| Dec. 13, 2010 | (CN) | 2010 2 0653955 U |

(51) Int. Cl.
G01N 15/08 (2006.01)
G01N 35/00 (2006.01)
(52) U.S. Cl.
CPC .......... *G01N 35/00871* (2013.01); *G01N 15/08* (2013.01); *G01N 2035/00881* (2013.01)
(58) Field of Classification Search
CPC ............ G01N 15/08; G01N 35/00871; G01N 2035/00881
USPC ............................................... 73/866; 702/62
See application file for complete search history.

(56) References Cited

U.S. PATENT DOCUMENTS 7,034,707 B2 * 4/2006 Aisa ............................. 340/662
(Continued)

FOREIGN PATENT DOCUMENTS

CN 2859509 Y 1/2007
(Continued)

OTHER PUBLICATIONS

Aug. 11, 2011 Written Opinion of the International Searching Authority issued in International Patent Application No. PCT/CN2011/000367 (with translation).
(Continued)

*Primary Examiner* — Lisa Caputo
*Assistant Examiner* — Jonathan Dunlap
(74) *Attorney, Agent, or Firm* — Oliff PLC

(57) ABSTRACT

A material property testing device with capabilities of energy-consumption monitoring and environment detecting the device including a processing unit, which intercommunicates with the testing unit and the storage unit; the input end of the processing unit connects with an energy monitoring device and an environment detecting unit; the energy monitoring device is installed in a power supply module to monitor the electricity consumption conditions and sends the energy consumption data to the processing unit; the environment detecting unit adopts a detection sensor to detect the environment conditions and sends the environmental information to the processing unit.

11 Claims, 3 Drawing Sheets

(56) References Cited

U.S. PATENT DOCUMENTS

Figure 1:
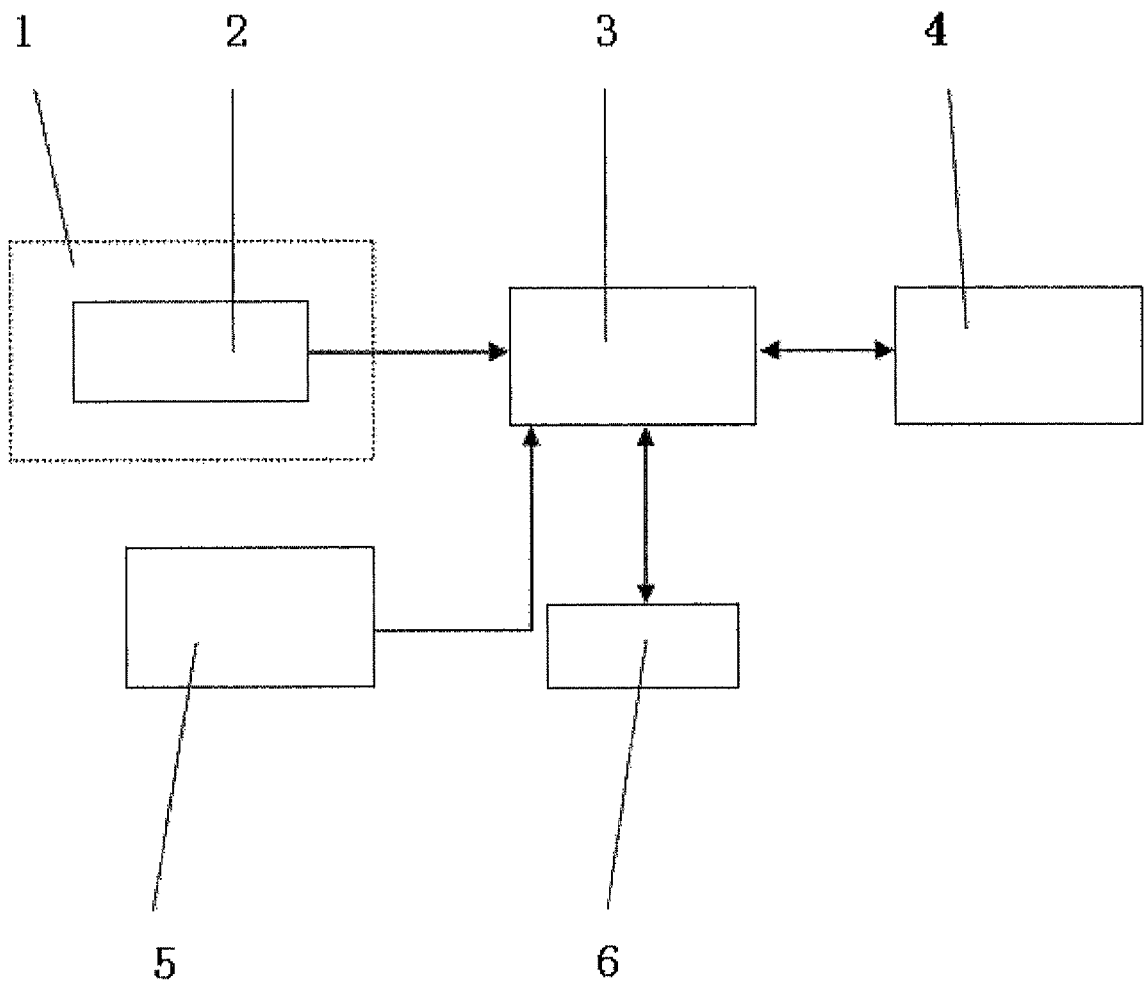

2004/0129890 A1* 7/2004 Berman et al. ............... 250/380
2005/0017602 A1* 1/2005 Arms et al. .................. 310/339
2009/0289615 A1* 11/2009 Foley ........................... 323/318
2010/0332164 A1* 12/2010 Aisa et al. ..................... 702/62

FOREIGN PATENT DOCUMENTS

| CN | 101055242 A | 10/2007 |
| CN | 101285762 A | 10/2008 |
| CN | 201538021 U | 8/2010 |
| CN | 101975712 A | 2/2011 |
| CN | 101975719 A | 2/2011 |
| CN | 101975720 A | 2/2011 |
| CN | 101975736 A | 2/2011 |
| JP | 2005-351661 | 12/2005 |

OTHER PUBLICATIONS

Aug. 11, 2011 International Search Report issued in International Patent Application No. PCT/CN2011/000367.

* cited by examiner

MATERIAL PROPERTY TESTING DEVICES WITH CAPABILITIES OF MONITORING ENERGY-CONSUMPTION AND DETECTING THE ENVIRONMENT

BACKGROUND

1. Field of Invention

The invention relates to a type of material property testing device with capabilities of monitoring energy-consumption and detecting the environment.

2. Description of Related Art

As a result of the earth energy shortage, the aggravation of environmental pollution and the social recognition of low-carbon economy, how can laboratory staff use laboratory equipments and resources reasonably, effectively and economically has become a major concern, and the monitoring of equipment energy consumption is a prerequisite for realizing economical usage. At present, while it is relatively easy to monitor the overall energy consumption of the laboratory, it is much more difficult to monitor the energy consumption of individual equipment. As for current material property testing devices, they cannot provide accurate energy consumption information during the operation.

As technologies develop continuously, the manufacturing and R&D of packaging materials are developing towards lighter, thinner, more convenient and more economical direction. The extensive application of functional materials and the importance of material property testing becomes more and more prominent. also the requirements on material indexes are more and more stringent. For example, whether the water vapor transmission rate of certain materials meets the standard is the key for determining whether a large quantity of packaging materials are qualified or rejected; and adequate mechanical properties are the basis of the wide application of packaging materials. The impact of environmental factors on the test becomes more significant during the testing of these indicators, for example, the levelness of the device can generate great influence on the testing data of certain mechanical properties; temperature is an important factor that affects the barrier property of materials; the influence of vibration on thickness measurement cannot be neglected; and the environment humidity and other environmental factors can also place certain impact on the test. Therefore these factors deserve particular attention and should be recorded for data analysis. At present, material property testing devices cannot detect these environmental factors, so the environmental condition during testing cannot be accurately obtained or recorded. Thereby the testing personnel cannot determine whether the testing process is normal or not, and further validation can only be done through increasing the test quantity.

In addition, the testing items on packaging materials nowadays increase greatly, consequently errors occurring during the manual input of specimen information and the manual collection of testing data also increase, which renders data accuracy at risk and brings about a huge amount of work for review. Furthermore, the current data collection method is time-consuming and inefficient, and has become a prominent problem restricting testing efficiency.

Clearly, for the present material property testing devices, the lack of equipment energy-consumption monitoring and the deficiency of environmental monitoring have become outstanding problems that restrict the development of such tests and affect test accuracy. The low degree of automation of devices data transfer should also be solved to lay the foundation for building informationalized testing systems in the future.

SUMMARY OF THE INVENTION

The invention comprises a material property testing device with capabilities of monitoring energy-consumption and detecting the environment to overcome the above deficiency of existing technology. The device has capabilities of monitoring energy-consumption and detecting environment. Meanwhile, the device has capabilities of collecting specimen information, sending and receiving data, thereby achieving the monitoring and recording of electricity usage conditions and testing environment conditions for the device, and achieving the collection of specimen information. At the same time, the data is transmitted from the processing unit to an external information server via the communication unit. The objective of the invention is achieved by adopting the following technical solution:

A material property testing device with capabilities of energy-consumption monitoring and environment detecting comprises a processing unit, which intercommunicates with the testing unit and the storage unit; the input end of the processing unit also connects with an energy monitoring device and an environment detecting unit respectively; The energy monitoring device is installed in a power supply module and connects with the processing unit to monitor the electricity consumption conditions and sends the energy consumption data to the processing unit; the environment detecting unit uses a detection sensor to detect the environmental conditions and sends the environmental information to the processing unit.

The aforementioned processing unit also connects with the communication unit I.

The aforementioned communication unit I comprises an input module and an output module. The input module connects with a label information acquisition device via networks. And the output module connects with an information server via networks. The label information acquisition device sends the sample information to the processing unit via the input module of the communication unit I. The testing data are sent to the processing unit via the testing unit after the test completes. The processing unit summarizes and sends the sample information and the testing data to the storage unit for storing and sends the summarized information to the information server via the output module of the communication unit I.

The label information acquisition device and the information server both have independent data sending and receiving devices.

The testing unit refers to at least one of the following: weighing method water vapor permeability testing unit, sensor method water vapor permeability testing unit, equal-pressure method gas permeability testing unit, differential-pressure method gas permeability testing unit, thickness testing unit, dart impact testing unit, pendulum mass impact testing unit, heat-seal testing unit, coefficient of friction testing unit, tearing force testing unit, force and strength testing unit, thermal shrinkage testing unit, hot tack testing unit, gradient heat seal testing unit, headspace gas analyzing testing unit, flex durability testing unit, seal testing unit, or leakage testing unit.

The energy monitoring device refers to at least one of the following: current sensor and voltage sensor, or smart ammeter.

The environment detecting unit comprises at least one detection sensor. The detecting sensor refers to at least one of the following: temperature sensor, humidity sensor, vibration sensor, inclination sensor, or hazard gas sensor.

The label information acquisition device refers to at least one of the following: electronic tag reader, bar code reader, or information recording instrument.

The network refers to at least one of the following: cable network, wireless network, or wireless communication network.

The information server refers to at least one of server or computer.

The material property testing device in this invention comprises five parts which include a processing unit, a testing unit, a storage unit, an energy monitoring device and an environment detecting unit. The processing unit intercommunicates with the testing unit and the storage unit. The output end of the energy monitoring device and the output end of the environment detecting unit connect with the input end of the processing unit. The energy monitoring device is installed in the power supply module of the material property testing device to monitor the electricity consumption conditions of the material property testing device and send the energy consumption data to the processing unit. The energy monitoring device refers to at least one of the following: current sensor and voltage sensor, or smart ammeter. The environment detecting unit comprises at least one detection sensor. The environment detecting unit uses the detection sensor to detect the environment conditions and sends the environmental information to the processing unit. The detection sensor involved refers to at least one of the following: temperature sensor, humidity sensor, vibration sensor, inclination sensor, or hazard gas sensor. When the test is conducted, the test specimen is put into the measuring device controlled by the testing unit within the material property testing device as requested for the test to begin. Then the processing unit sends a test starting signal to the testing unit. The testing unit then completes the test and sends the testing data to the processing unit. The energy monitoring device and the environment detecting unit then send the electricity consumption data and the environmental information to the processing unit according to settings. The processing unit summarizes the energy consumption data, the environmental information and the testing data, and performs an overall data analysis according to the requirements of the settings, and then sends the summarized data and the analysis results to the storage unit for storing.

The present invention also provides another structure which can achieve the data exchange between the material property testing device and external devices, and the collection of specimen information. The material property testing device comprises six parts which include a processing unit, a testing unit, a storage unit, an energy monitoring device, an environment detecting unit and a communication unit I. Meanwhile, a label information acquisition device and an information server are needed for achieving the specimen information collection and the data exchange between the material property testing device and external devices. The processing unit intercommunicates with the testing unit, the storage unit and the communication unit I respectively. The output end of the energy monitoring device and the output end of the environment detecting unit connect with the input end of the processing unit. The material property testing device connects with the label information acquisition device and the information server respectively via cable networks, wireless networks or wireless communication networks. The energy monitoring device is installed in the power supply module of the material property testing device to monitor the electricity consumption conditions of the material property testing device and send the energy consumption data to the processing unit. This energy monitoring device refers to at least one of the following: current sensor and voltage sensor, or smart ammeter. The environment detecting unit has at least one detection sensor. The environment detecting unit uses the detection sensor to detect environment conditions and sends the environmental information to the processing unit. The detection sensor refers to at least one of the following: temperature sensor, humidity sensor, vibration sensor, inclination sensor, or hazard gas sensor. The communication unit I comprises an input module and an output module. The input module connects with the label information acquisition device via cable networks, wireless networks or wireless communication networks. And the output module connects with the information server via cable networks, wireless networks or wireless communication networks. The label information acquisition device is an information collecting device, which matches with the information pattern set on the specimen label and can collect the specimen information in the label, and send the specimen information to the processing unit via the input module of the communication unit I. After the test completes, the testing unit sends the testing data to the processing unit. The processing unit summarizes and sends the specimen information and the testing data to the storage unit for storing, and to the information server via the output module of the communication unit I. When the test is conducted, firstly, the label information acquisition device collects the material and manufacture information in the specimen label and sends this information to the processing unit via the input module of the communication unit I. Then, the corresponding specimen are put into the measuring device controlled by the testing unit within the material property testing device as requested for the test to begin. The processing unit then sends a testing starting signal to the testing unit. The testing unit then completes the test and sends the testing data to the processing unit. The energy monitoring device and the environment detecting unit then send the electricity consumption data and the environmental information to the processing unit according to settings. The processing unit summarizes the energy consumption data, the environmental information generated during the test and the specimen testing data, and completes the overall data analysis according to the settings, and then sends the summarized data and the analysis results to the storage unit for storing and to the information server via the output module of the communication unit I. The label information acquisition device and the information server both have independent data sending and receiving devices. The label and the label information acquisition device are respectively: electronic label and electronic label reader; or bar code label and bar code reader; or handwritten label and information recording instrument. The information server refers to at least one of server or computer.

The advantages of this invention are as follows:
1. The workload of laboratory network construction can be reduced.
2. Historical detection data of the laboratorial environment can be saved, which facilitates the developing and passing of laboratory certification.
3. Laboratory safety can be effectively ensured through detecting the laboratorial environment.
4. Test data validity can be accurately determined, thereby achieving error correction analysis of the test data.
5. The test effectiveness can be managed and the use efficiency of instruments can be analyzed.
6. Laboratory energy consumption can be managed.
7. An embedded computer module can be used as the processing unit to improve system security and stability.

8. It has good expandability, and can achieve smooth data exchange with a large number of electronic products, which lays a foundation for the digital information communication in the future.
9. Providing a high degree of automation for the specimen information acquisition and data transmission, which ensure the accuracy of data and specimen information.
10. Mass data storage at a high speed can be achieved, thereby breaking through the limit of single machine storage, and laying the foundation for providing product quality analysis reports for any sections.
11. Providing great convenience for specimen information acquisition, and effectively improving efficiency and significantly lowering time consumption.
12. Realizing the remote control of tests.

BRIEF DESCRIPTION OF THE DIAGRAMS

Figure 2:
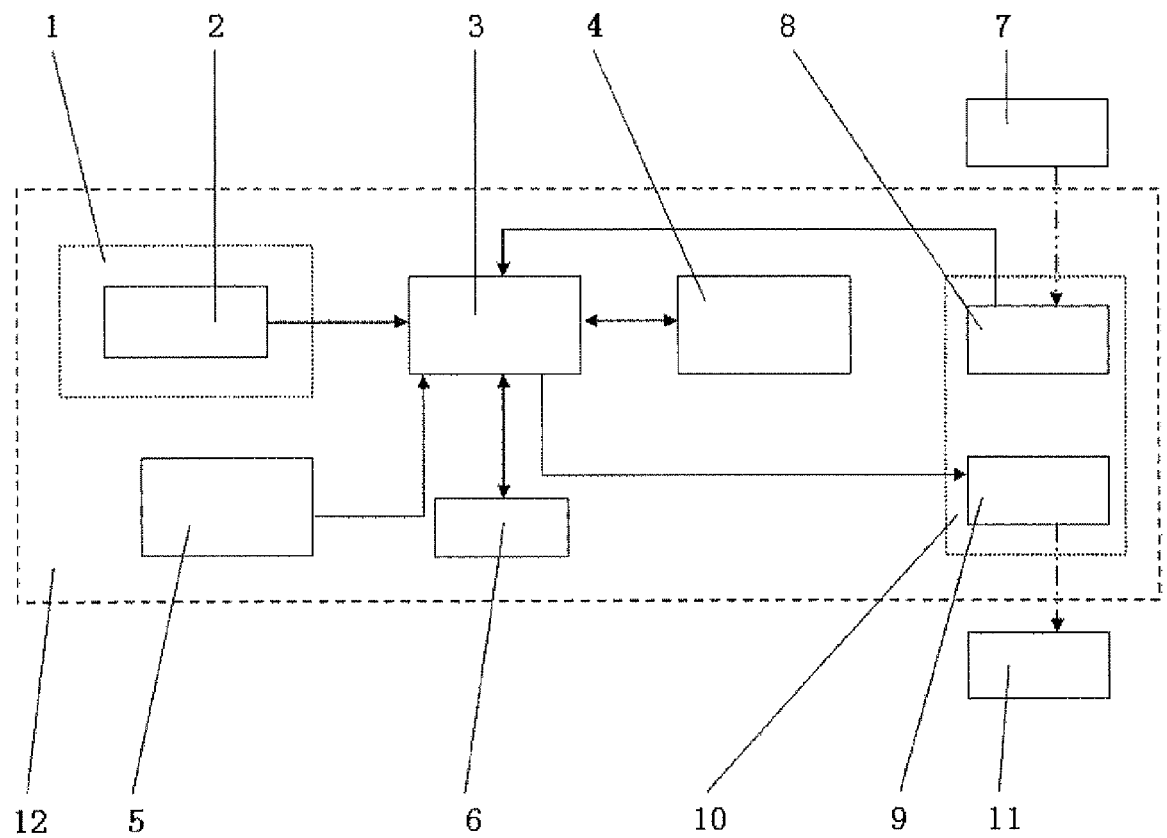
Figure 3:
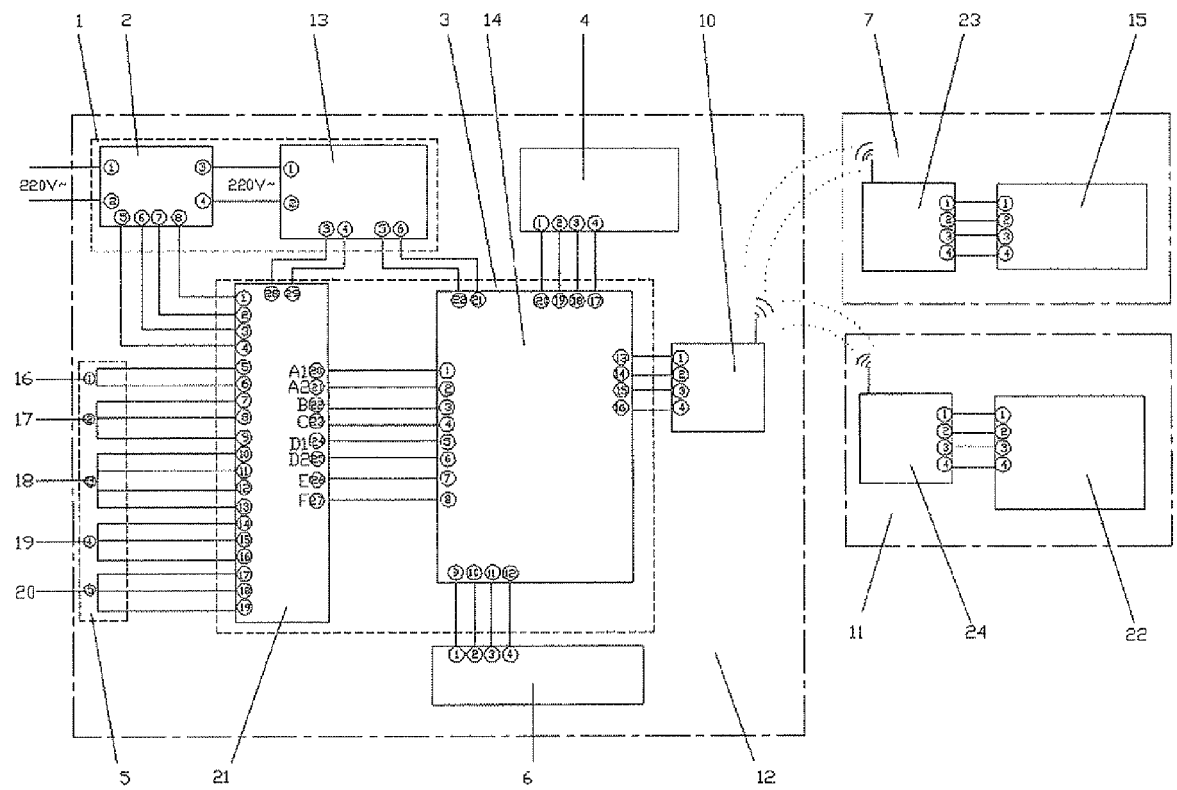

FIG. 1 is a diagrammatic representation of the invention;
FIG. 2 is a diagrammatic representation of an alternative form of the invention;
FIG. 3 is the electrical diagram of the invention.
Wherein, 1. Power supply module; 2. Energy monitoring device; 3. Processing unit; 4. Testing unit; 5. Environment detecting unit; 6. Storage unit; 7. Label information acquisition device; 8. Input module; 9. Output module; 10. Communication unit I; 11. Information server; 12. Material property testing device; 13. AC-DC power supply module; 14. Main control module; 15. Electronic label reader; 16. Temperature sensor; 17. Humidity sensor; 18. Inclination sensor; 19. Vibration sensor; 20. Hazard gas sensor; 21. Analog-digital converter; 22. Terminals; 23. Communication unit II; 24. Communication unit III.

DETAILED DESCRIPTION

The invention is further illustrated with the attached diagrams and embodiments.

Embodiment 1

In FIG. 1, the material property testing device in the invention comprises five parts which include a processing unit 3, a testing unit 4, a storage unit 6, an energy monitoring device 2 and an environment detecting unit 5. The processing unit 3 intercommunicates with the testing unit 4 and the storage unit 6. The output end of the energy monitoring device 2 and the output end of the environment detecting unit 5 communicate with the input end of the processing unit 3. The energy monitoring device 2 is installed in the power supply module 1 of the material property testing device to monitor the electricity consumption conditions of the material property testing device and send the energy consumption data to the processing unit 3. The energy monitoring device 2 refers to at least one of the following: current sensor and voltage sensor, or smart ammeter. The environment detecting unit 5 comprises at least one detection sensor. The environment detecting unit 5 uses the detection sensor to detect the environmental conditions and send the environmental information to the processing unit 3. The detection sensor refers to at least one of the following: temperature sensor, humidity sensor, vibration sensor, inclination sensor, or hazard gas sensor. When the test is conducted, the test specimen is put into the measuring device controlled by the testing unit 4 within the material property testing device as requested for the test to begin. Then the processing unit 3 sends a test starting signal to the testing unit 4. The testing unit 4 then completes the test and sends the testing data to the processing unit 3. The energy detecting device 2 and the environment monitoring unit 5 then send the electricity consumption data and the environmental information to the processing unit 3 according to settings. The processing unit 3 summarizes the energy consumption data, the environmental information and the testing data, and completes the overall data analysis according to the settings, and then sends the summarized data and the analysis results to the storage unit 6 for storing.

Embodiment 2

In FIG. 2, the material property testing device 12 of the invention comprises six parts which include a processing unit 3, a testing unit 4, a storage unit 6, an energy monitoring device 2, an environment detecting unit 5 and a communication unit I 10. Meanwhile, a label information acquisition device 7 and an information server 11 are needed for achieving the specimen information collection and the data exchange between the material property testing device 12 and external devices. The processing unit 3 intercommunicates with the testing unit 4, the storage unit 6 and the communication unit I 10 respectively. The output end of the energy monitoring device 2 and the output end of the environment detecting unit 5 connects with the input end of the processing unit 3. The material property testing device 12 connects with the label information acquisition device 7 and the information server 11 via cable networks or wireless networks or wireless communication networks. The energy monitoring device 2 is installed in the power supply module 1 of the material property testing device 12 to monitor the electricity consumption conditions of the material property testing device 12 and send energy consumption data to the processing unit 3. The energy monitoring device 2 refers to at least one of the following: current sensor and voltage sensor, or smart ammeter. The environment detecting unit 5 includes at least one detection sensor. The environment detecting unit 5 uses the detection sensor to detect the environmental conditions and sends the environmental information to the processing unit 3. The detection sensor refers to at least one of the following: temperature sensor, humidity sensor, vibration sensor, inclination sensor or hazard gas sensor. The communication unit I 10 comprises an input module 8 and an output module 9. The input module 8 connects with the label information acquisition device 7 via cable networks or wireless networks or wireless communication networks. And the output module 9 connects with the information server 11 via cable networks or wireless networks or wireless communication networks. The label information acquisition device 7 refers to an information collecting device matched with the information pattern set on the sample label and can collect the sample information in the labels, afterwards sends the sample information to the processing unit 3 via the input module 8 of the communication unit I 10. When the test completes, the testing unit 4 sends the testing data to the processing unit 3, the processing unit 3 summarizes the sample information with the testing data, and then sends to the storage unit 6 for storing, and sends the summarized information to the information sever 11 via the output module 9 of the communication unit I 10. When the test is conducted, firstly, the label information acquisition device 7 collects the material and manufacture information in the specimen label and sends this information to the processing unit 3 via the input module 8 of the communication unit I 10. Then, the corresponding specimen are put into the measuring device controlled by the testing unit 4 within the material property testing device 12 as requested for the test to begin. The processing unit 3 then sends a testing starting signal to the testing unit 4. The testing unit 4 then completes test and sends the testing data to the processing unit 3. The energy monitoring device 2 and the environment detecting unit 5 then send the electricity consumption data and the environmental information to the processing unit 3 according to settings. The processing unit 3 summarizes the energy consumption data, the environmental information generated during the test and the specimen testing data and completes the overall data analysis according to the settings, and then sends the summarized data and the analysis results to the storage unit 6 for storing and to the information server 11 via the output module 9 of the communication unit I 10. The label information acquisition device 7 and the information server 11 both have independent data sending and receiving devices. The label and label information acquisition device 7 are respectively: electronic label and electronic label reader; or bar code label and bar code reader; or hand-writing label and information recording instrument. The information server 11 refers to at least one of server or computer.

Embodiment 3

The embodiment provides a relationship of the circuit connection. The power supply module 1 comprises an energy monitoring device 2 (current transformer: TK1A5C5V2; voltage transformer: TK1A250V5V2) and an AC-DC power supply module 13 (WP75-TL) which are interconnected. The energy monitoring device 2 also connects with the analog-digital converter 21 (16 bits data acquisition board). The AC-DC power supply module 13 is the power supply transformer and connects with the main control module 14 (x86 low-power embedded motherboard) and the analog-digital converter 21. The processing unit 3 comprises a main control module 14 and an analog-digital converter 21 which are interconnected. The main control module 14 is used for logic control and data processing. It connects with the testing unit 4, the communication unit I10 (ZigBee wireless communication module) and the storage unit 6 (EEPROM 24C512). The analog-digital converter 21 completes the data acquisition and signal conversion. It connects with the temperature sensor 16 (PT100 platinum resistance or thermistor), the humidity sensor 17 (capacitive relative humidity sensor: Honeywell's HIH-4000), the inclination sensor 18 (dual-axis tilt sensor UFGeng), the vibration sensor 19 (accelerometer vibration sensor Model 1221), and the hazard gas sensor 20 (H2 sensor, CH4 sensor, etc.). The environment detecting unit 5 comprises a temperature sensor 16, a humidity sensor 17, an inclination sensor 18, a vibration sensor 19 and a hazard gas sensor 20. The label information acquisition device 7 (two-dimensional digital scanner Symbol) comprises an electronic label reader 15 (X86 low-power embedded motherboard) and a communication unit II23 (ZigBee wireless communication module) which are interconnected. The label information acquisition device 7 exchanges the specimen label information which is obtained by the electronic label reader 15 with the communication unit I10 via the communication unit II23. The information server 11 comprises terminals 22 and a communication unit III24 (ZigBee wireless communication modules) which are interconnected. The data in the information server 11 are stored in the terminals 22. The information server 11 exchanges information with the communication unit I10 via the communication unit III24. The communication unit I10, the communication unit II23 and the communication unit III24 all have data input and output functions.

The testing unit used in this invention refers to at least one of the following: weighing method water vapor permeability testing unit, sensor method water vapor permeability testing unit, equal-pressure method gas permeability testing unit, differential-pressure method gas permeability testing unit, thickness testing unit, dart impact testing unit, pendulum mass impact testing unit, heat-seal testing unit, coefficient of friction testing unit, tearing force testing unit, force and strength testing unit, thermal shrinkage testing unit, hot tack testing unit, gradient heat seal testing unit, headspace gas analyzing testing unit, flex durability testing unit, seal testing unit, or leakage testing unit. All the above units are existing equipments and can operate according to normal working modes during the test.

What is claimed is:

1. A material property testing device comprises a processing unit, a testing unit, a storage unit, an energy monitoring device and an environment detecting unit, wherein the processing unit intercommunicates with the testing unit and the storage unit, the input end of the processing unit connects with the energy monitoring device and the environment detecting unit, and the energy monitoring device is installed in a power supply module.

2. The material property testing device of claim 1, in which the processing unit connects with a communication unit I.

3. The material property testing device of claim 2, in which the communication unit I comprises an input module and an output module, the input module connects with a label information acquisition device via networks, and the output module connects with an information server via networks.

4. The material property testing device of claim 3, in which the label information acquisition device and the information server both have independent data sending and receiving devices.

5. The material property testing device of claim 4, in which the label information acquisition device refers to at least one of the following: electronic tag reader, bar code reader, or information recording instrument.

6. The material property testing device of claim 3, in which the label information acquisition device refers to at least one of the following: electronic tag reader, bar code reader, or information recording instrument.

7. The material property testing device of claim 3, in which the network refers to at least one of the following: cable network, wireless network, or wireless communication network.

8. The material property testing device of claim 3, in which the information server refers to at least one of server or computer.

9. The material property testing device of claim 1, in which the testing unit used in the invention refers to at least one of the following: weighing method water vapor permeability testing unit, sensor method water vapor permeability testing unit, equal-pressure method gas permeability testing unit, differential-pressure method gas permeability testing unit, thickness testing unit, dart impact testing unit, pendulum mass impact testing unit, heat-seal testing unit, coefficient of friction coefficient testing unit, tearing force testing unit, force and strength testing unit, thermal shrinkage testing unit, hot tack testing unit, gradient heat seal testing unit, headspace gas analyzing testing unit, flex durability testing unit, seal testing unit, or leakage testing unit.

10. The material property testing device of claim 1, in which the energy monitoring device refers to at least one of the following: current sensor and voltage sensor, or smart ammeter.

11. The material property testing device of claim 1, in which the environment detecting unit comprises at least one detection sensor, wherein the detection sensor refers to at least one of the following: temperature sensor, humidity sensor, vibration sensor, inclination sensor, or hazard gas sensor.

* * * * *